(12) United States Patent
Leipold et al.

(10) Patent No.: US 9,994,803 B2
(45) Date of Patent: Jun. 12, 2018

(54) BLOCK-SHAPED AGENT FOR APPLICATION ON A SANITARY OBJECT

(71) Applicant: GETing solutions GmbH, Herrenberg (DE)

(72) Inventors: Joachim Leipold, Reutlingen (DE); Edgar Jaeschke, Filderstadt (DE)

(73) Assignee: BUCK SERVICE GMBH, Herrenberg (DE)

( * ) Notice: Subject to any disclaimer, the term of this patent is extended or adjusted under 35 U.S.C. 154(b) by 235 days.

(21) Appl. No.: 14/417,381

(22) PCT Filed: Jul. 4, 2013

(86) PCT No.: PCT/EP2013/064125
§ 371 (c)(1),
(2) Date: Jan. 26, 2015

(87) PCT Pub. No.: WO2014/016098
PCT Pub. Date: Jan. 30, 2014

(65) Prior Publication Data
US 2015/0191683 A1  Jul. 9, 2015

(30) Foreign Application Priority Data
Jul. 25, 2012 (DE) ........................ 10 2012 106 742

(51) Int. Cl.
| | |
|---|---|
| *C11D 17/00* | (2006.01) |
| *A61L 2/232* | (2006.01) |
| *A61L 9/05* | (2006.01) |
| *C11D 3/22* | (2006.01) |
| *C11D 11/00* | (2006.01) |

(52) U.S. Cl.
CPC .......... *C11D 17/0056* (2013.01); *A61L 2/232* (2013.01); *A61L 9/05* (2013.01); *C11D 3/222* (2013.01); *C11D 11/0023* (2013.01); *C11D 17/0039* (2013.01)

(58) Field of Classification Search
None
See application file for complete search history.

(56) References Cited

U.S. PATENT DOCUMENTS

| | | | | |
|---|---|---|---|---|
| 5,336,427 | A * | 8/1994 | Bunczk | C11D 3/18 510/192 |
| 7,709,433 | B2 * | 5/2010 | Veltman | C11D 1/143 510/191 |
| 2007/0245470 | A1 * | 10/2007 | Nguyen | E03D 9/032 4/223 |

FOREIGN PATENT DOCUMENTS

| | | |
|---|---|---|
| DE | 10048887 A1 | 4/2002 |
| DE | 102004056554 A1 | 5/2006 |
| DE | 202007015317 U1 | 5/2008 |
| DE | 102008028138 A1 | 12/2009 |
| DE | 102010032417 A1 | 2/2012 |
| EP | 1318191 A1 | 6/2003 |

(Continued)

*Primary Examiner* — Necholus Ogden, Jr.
(74) *Attorney, Agent, or Firm* — Kriegsman & Kriegsman

(57) ABSTRACT

Agent for cleaning and/or deodorizing for use in the sanitary field which is used to adhere to a moistened surface of a sanitary object and gradually to dissolve as it is flushed with water, which agent includes a cleaning block including tensides (10), wherein the surface (12) of the cleaning block is sticky, or becomes sticky in the presence of water, wherein the block (10) has on at least one side of its surface (12) a coating (13) of powder particles (14) to a thickness between 5 μm and 800 μm.

20 Claims, 1 Drawing Sheet

(56) References Cited

FOREIGN PATENT DOCUMENTS

| WO | 9966017 A1 | 12/1999 |
|----|------------|---------|
| WO | 2008058853 A1 | 5/2008 |
| WO | 2009106220 A1 | 9/2009 |
| WO | 2012017276 A1 | 2/2012 |
| WO | 2012062914 A1 | 5/2012 |

* cited by examiner

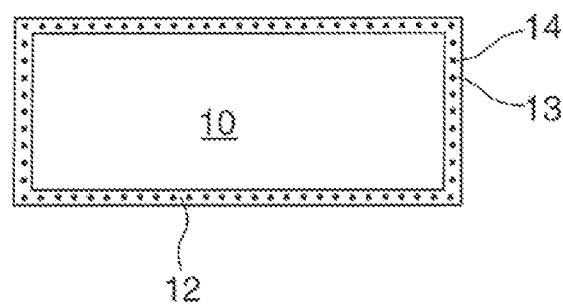

BLOCK-SHAPED AGENT FOR APPLICATION ON A SANITARY OBJECT

The present invention relates to a block-shaded agent for cleaning and/or deodorizing sanitary objects which can be stuck to a wet surface of a sanitary object, for example to a urinal, or under the rim of a toilet bowl, and gradually dissolves as it is flushed with water.

Viscous, generally pasty gels are known from the prior art which are applied from a corresponding container directly to the surface of the sanitary object, where they adhere and can be flushed away only after a relatively large number of flushing operations.

By virtue of the direct adhesion of the agent to the surface of the sanitary object, it is not necessary to provide additional containers such as the so-called. "WC cages", the use of which is perceived by the consumer as being unhygienic, especially when replacing the sanitary agent and when cleaning the toilet.

Such adhering viscous sanitary agent are described in WO 99/66017, DE 100 48 887 A1, EP 1 318 191 B1 or DE 10 2004 056 554 A1.

The known pasty, often gel-like toilet cleaning agent adhering to the sanitary surface can be applied either to a dry, or to a wet toilet surface easily, for example by means of a suitable applicator.

WO 2009/106220 furthermore describes pasty agent for the sanitary sector which are applied directly to a sanitary object, where they adhere and can only be flushed away after a relatively large number of flushing operations, where the agent are so sticky that they can serve for the attachment of block-shaped sanitary agent such as, for example, rim blocks. The application of the pasty "adhesive" can take place in the case of these agent directly to the dry sanitary object; wetting of the surface is not required.

Besides these pasty agent which can be applied directly to the wet or dry surface of the toilet, block-shaped toilet cleaners are also known from U.S. Pat. No. 7,709,433 B2. These agent, which are marketed in Germany under the trade name "00 WC Aktivstreifen", can be stuck onto a dry surface of sanitary objects by pressing. Upon flushing with water, the toilet cleaning blocks gradually dissolve—like the pastes described above—and release their active ingredients, surfactants, fragrances, etc.

These toilet cleaning blocks are not gel-like and comprise at least 25% solid anionic surfactants, between 1 and 25% by weight of liquid components and nonionic surfactants. The sticky block can have a film which is removed prior to the sticking to the surface of the sanitary object.

WO 2008/058853 teaches a solid cleaning agent block with a cleaning agent phase and an adhesive phase, where the adhesive phase comprises hydrophobic components and polymers, and the cleaning agent block serves for adhesion in a toilet bowl.

Furthermore, WO 2012/017276 A1 discloses agent for the sanitary sector which comprise a solid or semisolid active body with adhesion promoters which serves to adhere to the wall of the sanitary object, where the outer side of the block is covered at least partially with a water-soluble film. Preferably, the block is packaged entirely in the water-soluble film, and the film lies directly and tightly on the surface of the block.

In this way, the active body, a block, can be gripped using the hand and pressed against the wet toilet bowl without the user coming into contact with the components of the block. It is a further advantage that the covering does not have to be removed and possibly drops into the toilet or the block slips out of the hand upon taking it out of the packaging. The agent is intended to be pressed with the film to a wet surface, where firstly a first adhesion between wet surface and film should take place and the agent then sticks.

Although the agent covered with water-soluble film have the advantage that the agent can be gripped without a protective film having to be detached and disposed of correctly, it is, however, disadvantageous that the first adhesion via the film of the agent to the moistened mostly vertical surface at times inadequate, meaning that the block, drops into the bowl and is lost.

A further disadvantage of these agent is that the film closely covering the block and the shape of the block have to be matched to one another, meaning that blocks can only be provided in simple geometric shapes as a consequence of the limitation due to the film lying tightly on the surface.

The object of the invention consists in providing a sanitary agent that can be stuck directly on the moistened surface of a sanitary object and which exhibits improved adhesion and permits the adhesion of sanitary agent also with more complex geometries.

This object is achieved by a block-shaped agent for cleaning and/or deodorizing toilets which comprises a block with surfactants which has on at least one side of its surface a layer of powder particles of thickness between 5 μm and 800 μm, in particular less than 500 μm.

According to the invention, direct contact between the hand of the consumer and the block that becomes sticky on the surface of the sticky block or in a wet environment is prevented by the agent having a powder layer on at least one side of its surface. If the consumer touches the agent via this powder layer, then the hands are not contaminated.

However, compared to the water-soluble film known hitherto, the powder layer is more permeable and more "porous", and the powder particles can also be pushed against one another while pressing the agent against the surface. If the agent is pressed with the side having the powder layer against the surface of the moistened sanitary object, then the moisture passes much more quickly through the permeable powder layer onto the surface of the block, where the block then likewise starts to swell, and to adhere, than in the case of the polymer film known hitherto.

However, the powder layer also has a further advantage since when applying powder layers, one is independent on the geometry of the block, compared to a coating by means of a film. The powder must only be applied to the particular surface which, at the time of the coating operation, must have a stickiness such that an adequate amount of the powder adheres.

Generally, it is adequate if the powder layer covers the surface of the block to the extent that the consumer does riot contaminate his or her hands upon direct contact with the agent.

A suitable powder layer is generally any layer of a powder which, upon touching, is safe for the health of the consumer and which is not sticky, in particular does not adhere to the hands.

In the context of the present invention, powder is understood as meaning a form of the fragmentation of dry solid substances which is obtained as a result of comminution, i.e. pounding in a mortar or grinding in mills or cutting up or from punching or compression molds or as a consequence of spray or freeze dryings or crystallization from solutions. In the context of the invention, powders are either spherical or ellipsoidal as well as disk-shaped or differently shaped three-dimensional particles.

Powders that can be selected are, for example, natural or synthetic polymers such as celluloses, polysaccharides, polyacrylates, lignins, but also powder surfactants, thickeners, salts, silicates, sheet silicates, bentonites or Aerosils.

If the powders themselves are not hydrophilic, they merely form a permeable thin layer on the surface of the block, through whose many "openings" the moisture can then pass through to the surface of the block. As a result, of the water passing through to the surface of the block, the block swells slightly, i.e. the "smooth" powder layer is disturbed as a result of the swelling, and the surface becomes uneven as a result of the swelling and in some areas the adhesive mass of the block passes through to the surface of the agent such that upon pressing areas of the agent, there is direct contact between the adhering or the surface of the block that became sticky and the surface of the sanitary agent, thus facilitating good hold.

Preferably, the powder itself is water-soluble, water-swellable or water-dispersible. In this variant, the powder layer, upon contact with water, is either being dissolved itself, as a result of which areas of it are removed, thus facilitating direct contact between the surface of the block underneath, which is adherent or has become sticky due to contact with water, and the surface of the sanitary object and/or the powder swells, absorbs moisture and conveys this further to the surface of the block underneath, which then likewise swells. As a result of this, the surface of the agent in turn becomes uneven, and the sticky surface or the surface that became sticky of the block can again stick, in at least partial direct contact, to the surface of the sanitary object.

The fact that the powder particles and constituents of the block can be moved against each other in swollen layers upon pressing and thus sticky constituents of the block reach the surface of the sanitary object also contributes to the direct contact between the surface of the block and the surface of the sanitary object.

Preferably, the powders are selected from the group of natural and synthetic polymers, such as gelatin, the pectins, the celluloses, in particular sodium carboxymethylcellulose, hydroxyethylcellulose and hydroxypropylcellulose, the alginates, the (poly) saccharides, in particular starch, household sugars (icing sugar), flour, carob seed flour, guar seed flour, agar agar, gum arabic, the synthetic polymers such as the (alkoxylated) polyvinyl alcohols, polyvinylpyrrolidone, the diurethanes, the oleylamines, the block copolymers which comprise linked oligomers consisting of oligo- or polyethylene oxide and/or oligo- or propylene oxide and/or oligo- or polybutylene oxide, the powder surfactants and the thickeners xanthans, polybutadiene rubbers, polyisopropenes, the aryl ethoxylates or the alkyl aryl ethoxylates, the lignins.

Besides the organic powders, however, it is also possible to use inorganic powders, such as the swellable bentonites which are often used as thickeners, or water-soluble salts such as e.g. alkali, metal or alkaline earth metal salts, in particular of small particle size, or water-insoluble inorganic compounds such as silicates or Aerosils.

The powder layer used can also be powder mixtures.

The average particle size of the powder particles should be as small as possible in order to achieve a macroscopically extensive than coating with adequate adhesion of the powder to the surface of the block. Preferably, the average particle size of the powder particles should be less than or equal to 800 mm, preferably less than or equal to 700 mm, preferably less than 300 mm and particularly preferably less than 50 mm.

If nonhygroscopic powder particles or particles that do not rapidly absorb water are used, then the average particle size should be as small as possible and/or the particles should be flat.

If, by contrast, the powder particles are hygroscopic, i.e. they "suck up" the water rapidly or if they are swellable, then as a rule powder particles of a somewhat larger average particle size can also be used.

The average layer thickness of the powder layer should be between 5 and 500 micrometers, preferably between 10 and 200 micrometers and particularly preferably between 20 and 100 micrometers, in order, on the one hand, to avoid contaminating the hands and, on the other hand, however, to also permit an adequate and sufficiently rapid transportation of the water from the surface of the sanitary object through the powder layer to the surface of the block.

The powder coating of the agent also facilitates the transportation of the agent during the production operation. The agent is also protected by the powder layer, for example from sticking to the packaging.

The thickness of the powder layer (and also the choice of powder) should be such that the amount of water usually adhering to the vertical wall of the inside of a toilet bowl after a flushing operation suffices to penetrate through the powder layer and to bring about a swelling of the surface of the block with the provision of adhesive sites associated Therewith if the powder layer is too thick, then too little water passes through the layer to the surface of the block. Such a agent would not have the desired adhesion.

The passage of the water from the surface of the sanitary object through the powder layer is further intensified if hygroscopic substances such as, for example, salts are present in the block which "suck" the water so to speak in the direction of the surface of the block.

So that the agent can be gripped from all sides, preferably not just one side of the block, in particular that with which the block is stuck to the surface of the sanitary object, is coated with the powder, but all sides carry a powder layer.

The block comprises surfactants which serve for cleaning. Surfactants which can be used are anionic, nonionic, cationic and amphoteric surfactants. Anionic and nonionic surfactants become sticky in the presence of water and thus make it possible, following the passage of water through the powder layer and/or dissolution or swelling of the powder layer, for sticky surfactants to stick to the surface of the sanitary object at least in places.

The anionic surfactants used are preferably one or more substances from the group of the salts of the carboxylic acids, the sulfuric acid half-esters and the sulfonic acids, preferably from the group of fatty acids, the fatty alkylsulfuric acids and the alkylarylsulfonic acids. Usually, the carbon chain distributions of the anionic surfactants are in the range from 6 to 40, preferably 8 to 30 and in particular 12 to 22 carbon atoms.

Carboxylic acids (C6-C22) in the form of their metal salts (preferably alkali metal salts) and the natural or synthetic mixtures thereof, and also alkali metal salts of the sulfuric acid half-esters and longer-chain alcohols can likewise be used as anionic surfactants.

A further class of anionic surfactants which can be used according to the invention is the alkali metal salts of the alkylethersurlfuric acids. Alkyl ether sulfuric acids are synthesized like the alkylsulfuric acids from fatty alcohols, which are reacted with ethylene oxide to give the relevant fatty alcohol ethoxylates. Instead of ethylene oxide, it is also possible to use propylene oxide. The subsequent sulfonation produces the alkylethersulfuric acids in question.

The alkali metal salts of the alkanesulfonic acids and olefinsulfonic acids can also be used as anionic surfactants in the context of the present invention. Alkanesulfonic acids can contain the sulfonic acid group terminally bonded (primary alkanesulfonic acids) or along the carbon chain (secondary alkanesulfonic acids). Typical representatives are alkylbenzenesulfonates, particularly preferably linear alkylbenzenesulfonates (LAS).

The aforementioned anionic surfactants, can be used in their neutralized or alone or in a mixture with one another.

Nonionic surfactants that can be used are alkoxylated, preferably euhoxylated, in particular primary alcohols having preferably 8 to 18 carbon atoms and on average 1 to 12 mol of ethylene oxide (EO) per mol of alcohol, in which the alcohol residue can be linear or preferably 2-methyl-branched and/or can contain linear and methyl-branched residue in a mixture, as are usually present in oxoalcohol residue. In particular, however, alcohol ethoxylates with linear residue from alcohols of native origin having 12 to 18 carbon atoms, e.g. from coconut, palm, tallow fatty or oleyl alcohol and on average 2 to 8 EO per mol of alcohol are preferred. In addition to these nonionic surfactants, it is also possible to use fatty alcohols with more than 12 EO. Examples thereof are tallow fatty alcohols with 14 EO, 25 EO, 30 EO or 40 EO.

Moreover, further nonionic surfactants that can be used are also alkylglycosides of the general formula alkyl-O(G), where alkyl is a primary straight-chain or methyl-branched, in particular 2-methyl-branched, aliphatic residue having 8 to 22, preferably 12 to 18, carbon atoms, and G is the symbol for a glycoside unit having 5 or 6 carbon atoms, preferably glucose.

A further class of preferably used nonionic surfactants which can either be used as the sole nonionic surfactant or in combination with other nonionic surfactants are alkoxylated, preferably ethoxylated or ethoxylated and propoxylated fatty acid alkyl esters, preferably having 1 to 4 carbon atoms in the alkyl chain, in particular fatty acid methyl esters. Nonionic surfactants of the amine oxide type, for example N-coco-alkyl-N,N-dimethylamine oxide and N-tallow-alkyl-N,N-dihydroxyethylamine oxide, or alkanolamides can also be used.

Furthermore, the block can also comprise fragrances which serve for room deodorization. In general, the fragrance content is between 0 and 40% by weight, preferably between 2 and 20% by weight and in particular between 3 and 5% by weight.

The block can moreover contain salts, via which the solubility can be controlled. As a consequence of the hygroscopicity of some salts, the water absorption of the block can be improved upon pressing the agent against the moistened surface.

The sticking effect of the block can be brought about not only via the surfactants present in the block, but also via other known adhesion promoters which are sticky with or without water.

The adhesion promoters can for example also be applied in the form of a paste to the surface of the block.

The block can of course comprise further customary constituents, such as dyes, bleaches, disinfectants, foamers, acids, extrusion auxiliaries or plasticizers.

The block can be transparent or light-scattering. Preferably, the block is an extruded shaped body of a cleaning agent.

The block can of course also be composed a plurality of layers, where the layers can be for example extruded, cast and/or pasty.

A semisolid block is understood as meaning a block which has a somewhat pasty consistency such that it can still be easily molded, but can nevertheless be portioned as a "lump" and also essentially retains its shape under the action of the flush water.

As a rule, for the block according to the invention, upon pressing it onto a wet surface, contact times of less than seven seconds, preferably less than five seconds and particularly preferably of three or less seconds are required in order to permit an adequate adhesion to a vertical surface.

For producing the agent according to the invention, it is important that at least the side of the block which is then coated with the powder has during the application of the powder layer, a stickiness such that the powder sticks to the surface of the block.

For this purpose, the block can either per se be "intrinsically" sticky, for example as a result of the fact that it is soft and, besides nonionic surfactants, also comprises adequate solvents (water, alcohols, perfume oils, etc.). For the coating, such an already stinky block can for example be rolled in the powder, or powder can be sprinkled onto the sticky surface of the block. Since the adhesion of the powder is achieved only by "sticking" to the sticky surface, the applied powder layer is generally thin.

If, however, the block is not "intrinsically" sticky, then it is necessary to firstly achieve a sticky surface before the powder is then applied in a further step. A (short-term) stickiness of the surface can be achieved by wetting the surface with water or a water-containing substance. The water makes the surfactants located in the block and on its surface sticky, meaning that the powder can be applied and optionally pressed on and adheres to the surface.

In a further alternative, the surface of the block can be heated, which likewise leads to slight tackiness.

In a further alternative, the block is wetted with a liquid surfactant such as, for example, triethanol ether sulfate. This likewise leads to a sticky surface, and then the powder layer is applied.

During application of the agent according to the invention, the agent is firstly pressed onto the previously moistened surface of the sanitary object, in particular against the inside of a toilet bowl below the rim and above the water level, as a result of which it even sticks to a vertical, wall on the inside of a toilet bowl.

The agent is now permanently attached and will be completely removed again from the surface of the sanitary object as a result of the fact that it is gradually dissolved upon flushing with water.

Upon pressing the agent, the water adhering to the surface of the sanitary object is pressed against the powder layer, the water passes in part through openings in the powder layer to the surface of the block, the block swells somewhat on its surface, adhesive sites are formed or are already present, as a result of the swelling and the pressing the powder layer is "torn open", the sticky surface of the block can come into direct contact with the surface of the sanitary object and thus bring about adhesion.

As a result of further flushing during use, new adhesive points are always initially "activated" on the surface of the block, for example as a result of the fact that further powder is dissolved or flushed away and new adhesive points are "activated" in the form of surfactants on the surface. If the swelling layer is adequate, the block remains stuck.

Compared to the water-soluble film used hitherto, the adhesion of the agent takes place much more quickly because, compared to the prior art, it is no longer necessary to wait until the film has been partially dissolved by the water.

Rather, a more rapid adhesion of the agent is achieved by the powder layer according to the invention, and the number of sanitary agent which end up in the bottom of the toilet as a result of excessively short contact times can be reduced considerably.

The invention will now be described in more detail by reference to a working example.

It shows:

FIG. 1 shows a schematic representation of a agent according to the invention in cross section.

The agent comprises a rectangular-shaped cleaning block 10. The entire surface 12 of the block 10 is coated with a layer 13 of powder particles 14.

1. Production of a Agent According to the Invention

Guide formulation for a cleaning block

TABLE 1

|  | % by weight |
| --- | --- |
| Anionic surfactant 1 | 20-30 |
| (Anionic) surfactant 2 | 0-8 |
| (Anionic) surfactant 3 | 0-10 |
| Sodium chloride | 15-25 |
| Sodium sulfate | 25-35 |
| Polyethylene glycol 6000 | <5 |
| Sodium carbonate peroxyhydrate | <5 |
| Perfume | <5 |

The cleaning block (rim block) is extruded, cut and then coated as follows with Keizan ASX, from Kelco, as powder particles.

The block according to the guide formulation (about 6 g, area 60×20 mm, height about 2 mm) is heated to T>90° C. and then rubbed on one side with Marlinat 22/90 T (trienhanol ether sulfate). The rubbed area is then sprinkled (sieve) with Kelzan ASX and the excess powder is removed by turning the block over.

The thus coated agent is then stuck onto a prewetted, vertical tile, pressed for three seconds and the block is then flushed with a jet of water.

The block slowly washes away over several days upon ever repeating flushing with water and dry periods in between.

2. Experiments with a Powder-coated Domestos Refill Block and Comparative Experiment with Block Packaged in PVA Film For the further experiments, a Domestos refill block, Art. No. 8717163372043, was cut into disks measuring 40×60×4 mm and then coated with different powders.

TABLE 2

|  | Powder | Particle size (about) | Observation | After flushing |
| --- | --- | --- | --- | --- |
| Domestos initial weight |  |  |  |  |
| 10.3 | NaCl salt | 0.7-0.125 mm | drops off | ./. |
| 8.3 | NaSO$_4$ | 0.5-0.05 mm | drops off | ./. |
| 11 | PVA powder (1) | ./. | holds after at the latest 3 s | remains in situ |
| 15.66 | without | ./. | holds after at the latest 3 s | slips off somewhat |
| 12.3 | Aerosil | 12 nm | holds after | remains in |

TABLE 2-continued

|  | Powder | Particle size (about) | Observation | After flushing |
| --- | --- | --- | --- | --- |
| Comparison | 200, Degussa |  | at the latest 3 s | situ |
| Film packaging (2) | — (PVA film) | — | holds after 5-9 s | remains in situ |

1. Kuraray Mowiol 4-88 G
2. W C Brush; Relevi; Art. No.: 8002100237890

Experiments 1 and 2 show that the agent coated according to the invention with powders adhere even after shorter times (presently about three seconds) upon pressing against a prewetted surface and therefore more rapidly than the Relevi block packaged in film packaging used in the comparative experiment, which requires a pressing time of from five to nine seconds.

These and further experiments moreover show that powders with small particle sizes are particularly suitable for the coating or else particles with larger particle sizes which are strongly hygroscopic.

Likewise suitable are flat particles since these adhere well to the surface of the agent since, upon the use thereof, the pathway of the water to the surface of the block is reduced compared to spherical particles.

3. Experiments with the Self-adhesive 00 Null Null WC Aktiv Streifen from S.C. Johnson & Son, Inc.

The further experiments were carried out with the 00 Null Null WC Aktiv Streifen, 9 g, from S.C. Johnson & Son., Inc. It is a self-adhesive strip which is sold covered on both sides with a protective film. For application, the protective film on one side is removed and the strip is stuck to the dry toilet bowl. The protective film on the other side is then likewise pulled off.

The removal of the second protective film following adhesion, however, leads to the strip stuck to the bowl being partially pulled off again since the adhesion of the strip to the protective film is high.

The table below shows the flush numbers and adhesion of such 4C strips with protective film or with the powder coated according to the invention (without protective film).

TABLE 3

| Coating | Number of flushes | Observation |
| --- | --- | --- |
| Without; Protective film on both sides | 100 | Upon removing the second protective film, the strip is partially pulled off again from the WC bowl. Following successful adhesion, the strip adheres very well for about 100 flushes |
| Kelzan ASX | 100 | The two protective films were removed and the strip was coated on both sides with Kelzan. The coated strip adheres well to the moistened surface. |
| Flour | 260 | Good adhesion to moistened surface |
| Icing sugar | 260 | Good adhesion to moistened surface |
| Kelzan AR | 90 | Good adhesion to moistened surface |
| Kelzan AP | 90 | Good adhesion to moistened surface |

TABLE 3-continued

| Coating | Number of flushes | Observation |
|---|---|---|
| Kelcogel AFT | 90 | Good adhesion to moistened surface |
| Kelcogel LT 100 | 90 | Good adhesion to moistened surface |

The Kelzans were acquired from Kelco (www.cpkelco.com). Keizans are differently modified xanthans.

The experiments with the adhering WC strip show that the strips with the coatings according to the invention on the "sticky" side in the direction of the bowl exhibit a good adhesion to a moistened surface. The drying (off) of the surface otherwise required before the adhesion in the case of such strips—this is perceived by the consumer as unhygienic—is thus not necessary.

Furthermore, the experiments show that by coating the other side of the strip (directed to the consumer), a further advantage can be achieved since the coating material does not—like the protective film—have to he pulled off again and thus does not lead to partial detachment of the stuck-on strip again

The invention claimed is:

1. An agent for cleaning and/or deodorizing for the sanitary sector, which serves to adhere to a moistened surface of a sanitary object and to gradually dissolve as it is flushed with water, which agent comprises at least two layers of different composition, wherein a first layer of said at least two layers comprises a cleaning block, the cleaning block comprising surfactants, wherein the cleaning block is sticky on its surface or becomes sticky in the presence of water,
and wherein a second layer of said at least two layers is a layer of powder particles, wherein the second layer is permeable to moisture, and wherein the powder particles of the second layer are movable relative to one another upon an application of pressure to the second layer, whereby an increase in permeability of the second layer to moisture occurs, the second layer having a thickness of between 5 μm and 800 μm and being disposed on at least one side of the surface of the first layer.

2. The agent as claimed in claim 1, characterized in that the powder particles are selected from the group of celluloses, polysaccharides, synthetic or natural polymers, powder surfactants, thickeners, polybutadiene rubbers, polyisopropenes, block copolymers which comprise linked oligomers consisting of oligo- or polyethylene oxide and/or oligo- or propylene oxide and/or oligo- or polybutylene oxide, aryl ethoxylates or alkyl aryl ethoxylates, lignins, salts, silicates, sheet silicates or Aerosils.

3. The agent as claimed in claim 2, characterized in that the synthetic or natural polymers are polyacrylates, polysaccharides, (alkoxylated) polyvinyl alcohols, polyvinylpyrrolidone, alginates, diurethanes, gelatin, pectins or oleylamines.

4. The agent as claimed in claim 2, characterized in that the thickeners are bentonites and xanthans.

5. The agent as claimed in claim 1, characterized in that the particles are water-soluble or swellable or dispersible in water.

6. The agent as claimed in claim 1, characterized in that the second layer is less than 500 μm in thickness.

7. The agent as claimed in claim 6, characterized in that the second layer is between 10 μm and 200 μm in thickness.

8. The agent as claimed in claim 6, characterized in that the second layer is between 20 μm and 100 μm in thickness.

9. The agent as claimed in claim 1, characterized in that the average particle size of the powder particles is less than or equal to 800 μm.

10. The agent as claimed in claim 9, characterized in that the average particle size of the powder particles is less than or equal to 700 μm.

11. The agent as claimed in claim 9, characterized in that the average particle size of the powder particles is less than 300 μm.

12. The agent as claimed in claim 9, characterized in that the average particle size of the powder particles is less than 50 μm.

13. The agent as claimed in claim 1, characterized in that the cleaning block comprises salts.

14. The agent as claimed in claim 13, characterized in that the salts are soluble alkali metal or alkaline earth metal salts.

15. The agent as claimed in claim 1, characterized in that upon pressing the agent onto a wet surface, contact times of less than seven seconds are required in order to achieve adequate adhesion to a vertical surface.

16. The agent as claimed in claim 15, characterized in that upon pressing the agent onto a wet surface, contact times of less than five seconds are required in order to achieve adequate adhesion to a vertical surface.

17. The agent as claimed in claim 15, characterized in that upon pressing the agent onto a wet surface, contact times of less than three or less seconds are required in order to achieve adequate adhesion to a vertical surface.

18. A method for producing an agent as claimed in claim 1, characterized in that powder is applied to at least one sticky side of a block comprising surfactants.

19. The method as claimed in claim 18, characterized in that the side of the block to be coated is firstly made sticky prior to the coating by applying water, a water-containing substance, by heating or by smearing with liquid surfactants.

20. The agent as claimed in claim 1, wherein the second layer is disposed on all sides of the first layer.

* * * * *